(12) United States Patent
Chennubhotla et al.

(10) Patent No.: US 11,983,943 B2
(45) Date of Patent: May 14, 2024

(54) COMPUTATIONAL SYSTEMS PATHOLOGY SPATIAL ANALYSIS PLATFORM FOR IN SITU OR IN VITRO MULTI-PARAMETER CELLULAR AND SUBCELLULAR IMAGING DATA

(71) Applicant: UNIVERSITY OF PITTSBURGH-OF THE COMMONWEALTH SYSTEM OF HIGHER EDUCATION, Pittsburgh, PA (US)

(72) Inventors: Srinivas C. Chennubhotla, Pittsburgh, PA (US); Filippo Pullara, Pittsburgh, PA (US); Douglass L. Taylor, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 384 days.

(21) Appl. No.: 17/413,971

(22) PCT Filed: Dec. 16, 2019

(86) PCT No.: PCT/US2019/066446
§ 371 (c)(1),
(2) Date: Jun. 15, 2021

(87) PCT Pub. No.: WO2020/131658
PCT Pub. Date: Jun. 25, 2020

(65) Prior Publication Data
US 2022/0044401 A1    Feb. 10, 2022

Related U.S. Application Data

(60) Provisional application No. 62/781,759, filed on Dec. 19, 2018.

(51) Int. Cl.
*G06V 20/00* (2022.01)
*G01N 33/574* (2006.01)
(Continued)

(52) U.S. Cl.
CPC ......... *G06V 20/698* (2022.01); *G01N 33/574* (2013.01); *G06T 7/0012* (2013.01);
(Continued)

(58) Field of Classification Search
CPC .. G06V 20/698; G06V 10/426; G06V 10/761; G06V 2201/03; G01N 33/574;
(Continued)

(56) References Cited

U.S. PATENT DOCUMENTS

2010/0088264 A1  4/2010  Teverovskiy et al.
2010/0290692 A1  11/2010  Macaulay et al.
(Continued)

FOREIGN PATENT DOCUMENTS

JP  2018-525707 B2  9/2018
WO  2005/111905 A2  11/2005
(Continued)

OTHER PUBLICATIONS

Spagnolo et al. "Platform for Quantitative Evaluation of Spatial Intratumoral Heterogeneity in Multiplexed Fluorescence Images", Cancer Research, Nov. 1, 2017 (Nov. 1, 2017), vol. 77, 41-48 No. 21, pp. 71-74. (Year: 2017).*
(Continued)

*Primary Examiner* — Van D Huynh
(74) *Attorney, Agent, or Firm* — Philip E. Levy; Eckert Seamans Cherin & Mellott, LLC

(57) ABSTRACT

A computational systems pathology spatial analysis platform includes: (i) a spatial heterogeneity quantification component configured for generating a global quantification of spatial heterogeneity among cells of varying phenotypes
(Continued)

in multi-parameter cellular and subcellular imaging data; (ii) a microdomain identification component configured for identifying a plurality of microdomains for tissue samples based on the global quantification, each microdomain being associated with a tissue sample; and (iii) a weighted graph component configured for constructing a weighted graph for the multi-parameter cellular and subcellular imaging data, the weighted graph having a plurality of nodes and a plurality of edges each being located between a pair of the nodes, wherein in the weighted graph each node is a particular one of the microdomains and the edge between each pair of microdomains in the weighted graph is indicative of a degree of similarity between the pair of the microdomains.

18 Claims, 10 Drawing Sheets

(51) Int. Cl.
*G06T 7/00* (2017.01)
*G06V 10/426* (2022.01)
*G06V 10/74* (2022.01)
*G06V 20/69* (2022.01)

(52) U.S. Cl.
CPC .......... *G06V 10/426* (2022.01); *G06V 10/761* (2022.01); *G06T 2207/30024* (2013.01); *G06T 2207/30096* (2013.01); *G06V 2201/03* (2022.01)

(58) Field of Classification Search
CPC .................. G01N 33/48; G06T 7/0012; G06T 2207/30024; G06T 2207/30096; G06F 18/22; A61B 5/00
See application file for complete search history.

(56) References Cited

U.S. PATENT DOCUMENTS

| | | | | |
|---|---|---|---|---|
| 2013/0329973 A1* | 12/2013 | Cao | ....................... | G06T 7/0016 382/128 |
| 2014/0003702 A1* | 1/2014 | McCulloch | ........... | G06T 7/0012 382/133 |
| 2014/0024553 A1 | 1/2014 | Michalek et al. | | |
| 2014/0372450 A1* | 12/2014 | Graf | ......................... | G16B 5/00 707/742 |
| 2015/0169985 A1 | 6/2015 | Burger et al. | | |
| 2015/0310254 A1 | 10/2015 | Chennubhotla et al. | | |
| 2015/0347702 A1* | 12/2015 | Chukka | .................. | G16H 30/20 702/19 |
| 2016/0314580 A1* | 10/2016 | Lloyd | ........................ | G06T 7/11 |
| 2017/0046839 A1* | 2/2017 | Paik | ........................ | G06V 10/84 |
| 2017/0091527 A1* | 3/2017 | Sarachan | ........... | G06V 10/7715 |
| 2018/0239949 A1* | 8/2018 | Chander | ............... | G06F 18/214 |
| 2020/0302603 A1* | 9/2020 | Barnes | .................... | G06T 7/162 |
| 2021/0142908 A1* | 5/2021 | Lahrmann | .............. | G06V 10/82 |

FOREIGN PATENT DOCUMENTS

| | | |
|---|---|---|
| WO | 2017/142410 A1 | 8/2017 |
| WO | 2018/022548 A1 | 2/2018 |

OTHER PUBLICATIONS

Bulent Vener: "Cell-graphs", Communications of the ACM, Association for Computing Machinery, Inc, United States, vol. 60, No. 1, Dec. 20, 2016 (Dec. 20, 2016), pp. 74-84, XP058306178, ISSN: 0001-0782, DOI: 10.1145/2960404.

Spagnolo et al. "Platform for Quantitative Evaluation of Spatial Intratumoral Heterogeneity in Multiplexed Fluorescence Images," Cancer Research, Nov. 1, 2017 (Nov. 1, 2017), vol. 77, 41-48 No. 21, pp. 71-74. entire document.

Gallaher et al. "Spatial Heterogeneity and Evolutionary Dynamics Modulate Time to Recurrence in Continuous and Adaptive Cancer Therapies," Cancer Research, Jan. 30, 2018 (Jan. 30, 2018), vol. 78, No. 8, pp. 2127-2139. entire document.

Hao et al. "Spatial Intratumor Heterogeneity of Genetic, Epigenetic Alterations and Temporal Clonal Evolution in Esophageal Squamous Cell Carcinoma," Nat Genet, Oct. 17, 2016 (Oct. 17, 2016), vol. 48, No. 12, pp. 1500-1507. entire document.

Nguyen et al. "Spatial Statistics for Segmenting Histological Structures in H&E Stained Tissue Images," IEEE Trans Med Imaging, Mar. 16, 2017 (Mar. 16, 2017), vol. 36, No. 7, pp. 1522-1532. entire document.

* cited by examiner

COMPUTATIONAL SYSTEMS PATHOLOGY SPATIAL ANALYSIS PLATFORM FOR IN SITU OR IN VITRO MULTI-PARAMETER CELLULAR AND SUBCELLULAR IMAGING DATA

CROSS REFERENCE TO RELATED APPLICATIONS

This application is a U.S. National Stage Application under 35 U.S.C. § 371 of PCT International Application No. PCT/US2019/066446, filed on Dec. 16, 2019, entitled "Computational Systems Pathology Spatial Analysis Platform For In Situ or In Vitro Multi-Parameter Cellular And Subcellular Imaging Data," which claims priority under 35 U.S.C. § 119(e) from U.S. Provisional Patent Application No. 62/781,759, filed on Dec. 19, 2018, entitled "A Computational Systems Pathology Spatial Analysis Platform for In Situ Multi-parameter Cellular and Sub-Cellular Imaging Data," the contents of which are incorporated herein by reference.

BACKGROUND OF THE INVENTION

1. Field of the Invention

The present invention pertains to digital pathology, and, in particular, to a comprehensive computational systems pathology spatial analysis (CSPSA) computer platform capable of integrating, visualizing and modeling high dimensional in situ or in vitro cellular and subcellular resolved imaging data.

2. Description of the Related Art

Digital pathology refers to the acquisition, storage and display of histologically stained tissue samples and is initially gaining traction in niche applications such as second-opinion telepathology, immunostain interpretation, and intraoperative telepathology. Typically, a large volume of patient data, consisting of 3-50 slides, is generated from biopsy samples and is visually evaluated by a pathologist, under a microscope, but with digital technology by viewing on a high-definition monitor. Because of the manual labor involved, the current workflow practices are time consuming, error-prone and subjective.

Cancer is a heterogeneous disease. In hematoxylin and eosin (H&E) stained tissue images, heterogeneity is characterized by the presence of various histological structures, such as carcinoma in situ, invasive carcinoma, adipose tissue, blood vessels, and normal ducts. Moreover, for many malignancies, molecular and cellular heterogeneity is a prominent feature among tumors from different patients, between different sites of neoplasia in a single patient, and within a single tumor. Intratumor heterogeneity involves phenotypically distinct cancer cell clonal subpopulations and other cell types that comprise the tumor microenvironment (TME). These cancer cell clonal subpopulations and other cell types include local and bone marrow derived stromal stem and progenitor cells, subclasses of immune inflammatory cells that are either tumor promoting or tumor-killing, cancer associated fibroblasts, endothelial cells and pericytes. The TME can be viewed as an evolving ecosystem where cancer cells engage in heterotypic interactions with these other cell types and use available resources to proliferate and survive. Consistent with this perspective, the spatial relationships among the cell types within the TME (i.e., spatial heterogeneity) appear to be one of the main drivers of disease progression and therapy resistance. Thus, it is imperative to define the spatial heterogeneity within the TME to properly diagnose the specific disease sub-type and identify the optimal course of therapy for individual patients.

To date, intratumor heterogeneity has been explored using three major approaches. The first approach is to take core samples from specific regions of tumors to measure population averages. Heterogeneity in the samples is measured by analyzing multiple cores within the tumor using a number of techniques, including whole exome sequencing, epigenetics, proteomics, and metabolomics. The second approach involves "single cell analyses" using the above methods, RNASeq, imaging or flow cytometry after separation of the cells from the tissue. The third approach uses the spatial resolution of light microscope imaging to maintain spatial context, and is coupled with molecular-specific labels to measure biomarkers in the cells in situ. The biomarkers can identify cell type, state of activation (e.g. phosphorylation of target protein) and sub-cellular functions. These approaches, while each providing a certain level of effectiveness, all have various drawbacks and limitations.

In addition, one of the biggest challenges in assessing the clinical significance of tumor heterogeneity has been the lack of advanced tools for spatial analysis of multi-parameter cellular and subcellular imaging data.

SUMMARY OF THE INVENTION

In one embodiment, a method of analyzing disease progression from multi-parameter cellular and subcellular imaging data obtained from a plurality of tissue samples from a plurality of patients or a number of multicellular in vitro models is provided. The method includes generating a global quantification of a spatial heterogeneity among cells of certain varying predetermined phenotypes in the multi-parameter cellular and subcellular imaging data, identifying a plurality of microdomains for the plurality of tissue samples based on the global quantification, each microdomain being associated with a respective one of the tissue samples, and constructing a weighted graph for the multi-parameter cellular and subcellular imaging data. The weighted graph has a plurality of nodes and a plurality of edges each being located between a pair of the nodes, wherein in the weighted graph each node is a particular one of the microdomains and the edge between each pair of microdomains in the weighted graph is indicative of a degree of similarity between the pair of the microdomains.

In another embodiment, a computerized system for analyzing disease progression from multi-parameter cellular and subcellular imaging data obtained from a plurality of tissue samples from a plurality of patients or a number of multicellular in vitro models is provided. The system includes a processing apparatus that in turn includes: (i) a spatial heterogeneity quantification component configured for generating a global quantification of a spatial heterogeneity among cells of certain varying predetermined phenotypes in the multi-parameter cellular and subcellular imaging data; (ii) a microdomain identification component configured for identifying a plurality of microdomains for the plurality of tissue samples based on the global quantification, each microdomain being associated with a respective one of the tissue samples; and (iii) a weighted graph component configured for constructing a weighted graph for the multi-parameter cellular and subcellular imaging data, the weighted graph having a plurality of nodes and a plurality of edges each being located between a pair of the nodes, wherein in the weighted graph each node is a particular one of the microdomains and the edge between each pair of microdomains in the weighted graph is indicative of a degree of similarity between the pair of the microdomains.

In still another embodiment, a method of generating a representation of spatially informed heterocellular communication from multi-parameter cellular and subcellular imaging data obtained from a number of tissue samples from a number of patients or a number of multicellular in vitro models is provided. The method includes generating a quantification of a spatial heterogeneity among cells of certain varying predetermined phenotypes in the multi-parameter cellular and subcellular imaging data and identifying a microdomain for one of the tissue samples based on the quantification, including performing cell phenotyping on the multi-parameter cellular and subcellular imaging data to identify the certain varying predetermined phenotypes, and constructing a communications graph for the microdomain. Each of the phenotypes is a node in the communications graph, and an edge between each pair of the phenotypes in the communications graph is indicative of an influence of one phenotype in the pair on a presence of the other phenotype in the pair.

In yet another embodiment, a computerized system for generating a representation of spatially informed heterocellular communication from multi-parameter cellular and subcellular imaging data obtained from a number of tissue samples from a number of patients or a number of multicellular in vitro models is provided. The system includes a processing apparatus that includes (i) a spatial heterogeneity quantification component configured for generating a quantification of a spatial heterogeneity among cells of certain varying predetermined phenotypes in the multi-parameter cellular and subcellular imaging data, including performing cell phenotyping on the multi-parameter cellular and subcellular imaging data to identify the certain varying predetermined phenotypes, (ii) a microdomain identification component configured for identifying a plurality of microdomains for the number of tissue samples based on the based on the quantification, each microdomain being associated with one of the tissue samples, and (iii) a communication network component configured for constructing a communications graph for a selected one of the microdomains, wherein each of the phenotypes is a node in the communications graph, and wherein an edge between each pair of the phenotypes in the communications graph is indicative of an influence of one phenotype in the pair on a presence of the other phenotype in the pair.

In yet another embodiment, a method of creating a personalized medicine strategy for a specific patient, wherein the specific patient is one of a number of patients, and wherein the number of patients has associated therewith multi-parameter cellular and subcellular imaging data obtained from a number of tissue samples from the number of patients, is provided. The method includes identifying a plurality of microdomains in one of the tissue samples that is associated with the specific patient, wherein the plurality of microdomains are based on the multi-parameter cellular and subcellular imaging data, generating a heterocellular communication network for each of the microdomains, wherein each heterocellular communication network comprises a representation of spatially informed heterocellular communication for the microdomain, generating a quantification of an interdependence of the microdomains in space and time based on the heterocellular communication networks, and designing the medicine strategy for the specific patient based on the quantification.

In still another embodiment, a method of representing a time evolution of disease progression in a specific patient is provided, wherein the specific patient is one of a number of patients, and wherein the number of patients has associated therewith multi-parameter cellular and subcellular imaging data obtained from a number of tissue samples from the number of patients. The method includes generating a geometrical representation of a disease landscape for the specific patient, wherein the geometrical representation includes a plurality of points, wherein each point on the geometrical representation: (i) describes a disease status of the specific patient at a particular time and is based on a particular one of the tissue samples that is associated the selected patient, (ii) is based on a microdomain in the particular one of the tissue samples that is based on the multi-parameter cellular and subcellular imaging data, and (iii) includes a heterocellular communication network for the microdomain that comprises a representation of spatially informed heterocellular communication for the microdomain.

DETAILED DESCRIPTION OF EXEMPLARY EMBODIMENTS

Figure 1:
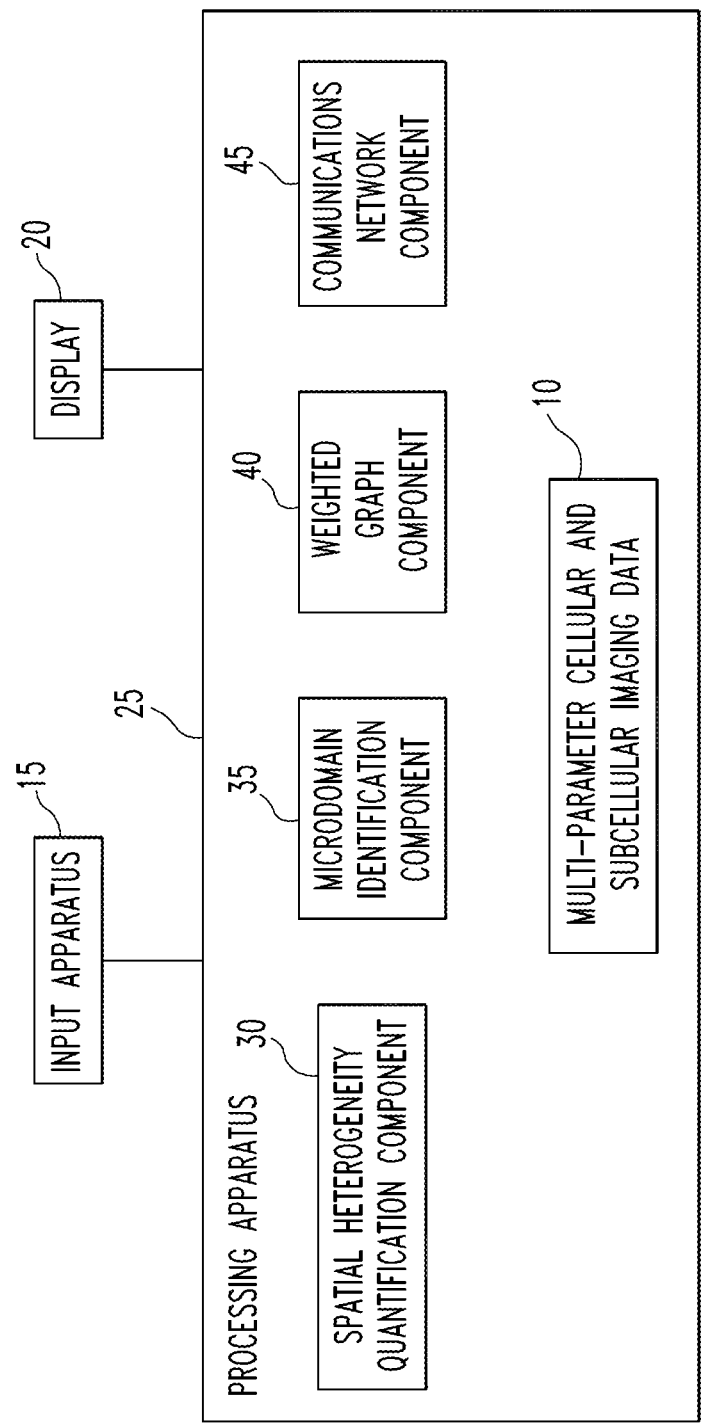
FIG. 1 is a schematic diagram of an exemplary computational systems pathology spatial analysis (CSPSA) platform for in situ or in vitro multi-parameter cellular and sub-cellular imaging data according to an embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described with respect to certain figures or graphs as screenshots, those skilled in the relevant art will recognize that various other alternatives can be employed.

As used herein, the term "multi-parameter cellular and subcellular imaging data" shall mean data obtained from generating a number of images from a number of a sections of tissue which provides information about a plurality of measurable parameters at the cellular or subcellular level in the sections of tissue. Multi-parameter cellular and subcellular imaging data may be created by a number of different imaging technologies, such as, without limitation, (1) transmitted light imaging with IHC using a number of biomarkers, (2) immunofluorescence imaging including both multiplexed imaging (1-7 biomarkers) and hyperplexed imaging (>7 biomarkers), (3) toponome imaging, (4) matrix-assisted laser desorption/ionization mass spectrometric imaging (MALDI MSI), (5) complementary spatial imaging, e.g., FISH, MxFISH, FISHSEQ, or CyTOF, (6) multiparameter ion beam imaging, and (7) in vitro imaging of experimental models. In addition, for example, and without limitation, multi-parameter cellular and subcellular imaging data may be created by generating a number of biomarker images from a number of a sections of tissue by labelling each section of tissue with multiple, different biomarkers.

As used herein, the term "spatial map" shall mean a representation, such as in a collection of data and/or a visually perceptible form, of a number of quantified spatial statistics that are indicative of the relationships among cells of varying predetermined phenotypes in a set of multi-parameter cellular and subcellular imaging data. For example, and without limitation, a spatial map may be a pointwise mutual information (PMI) map generated in the manner described in PCT Application No. PCT/US2016/036825 and United States Patent Application Publication No. 2018/0204085, both entitled "Systems and Methods for Finding Regions of Interest in Hematoxylin and Eosin (H&E) Stained Tissue Images and Quantifying Intratumor Cellular Spatial Heterogeneity in Multiplexed/Hyperplexed Fluorescence Tissue Images", the disclosures of which are incorporated herein by reference.

As used herein, the term "microdomain" shall mean a phenotypically distinct spatial arrangement (or motif) of phenotypic cells in a sample of tissue emerging from spatial intratumoral heterogeneity and associated with one or more outcome specific variables (e.g., time to recurrence). A microdomain may be identified from multi-parameter cellular and subcellular imaging data according to any of a number of known or hereafter developed methodologies such as, without limitation, the methodology that is described in detail in U.S. provisional application Ser. No. 62/675,832, entitled "Predicting the Recurrence Risk of Cancer Patients From Primary Tumors with Multiplexed Immunofluorescence Biomarkers and Their Spatial Correlation Statistics," and PCT Application No. PCT/US2019/033662, entitled "System and Method for Predicting the Risk of Cancer Recurrence From Spatial Multi-Parameter Cellular and Sub-Cellular Imaging Data for Tumors by Identifying Emergent Spatial Domain Networks Associated With Recurrence," each incorporated herein by reference, and/or in Spagnolo, et al., Platform for Quantitative Evaluation of Spatial Intratumoral Heterogeneity in Multiplexed Fluorescence Images, Cancer Res. 2017 Nov. 1; 77(21):e71-e74 and/or implemented in the public domain THRIVE (Tumor Heterogeneity Research Interactive Visualization Environment) software described in the above Spagnolo, et al reference. In that methodology, spatially resolved correlations between biomarkers as covariates in a multivariable survival model of outcome data (e.g., recurrence) are used to build a map for the spatial organization of cancer recurrence in a multiplexed tissue sample. These maps delineate microdomains associated with recurrence and metastatic progression.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject invention. It will be evident, however, that the disclosed concept can be practiced without these specific details without departing from the spirit and scope of this innovation.

The disclosed concept provides a comprehensive computational systems pathology spatial analysis (CSPSA) platform capable of integrating, visualizing and/or modeling high dimensional in situ cellular and sub-cellular resolved imaging data. The CSPSA platform of the disclosed concept combines a core set of existing tools for cell phenotyping and spatial analysis with an advanced toolset for inferring spatial heterocellular communication (cell-to-cell) and intracellular communication patterns, and for building tumor (or other disease) evolution trees from precancerous origins to metastasis end points in the case of cancer. Together these tools can be applied for both research and clinical purposes, such as quantifying spatial intratumoral heterogeneity in tissue samples and in vitro models, and correlating it with outcome data, building diagnostic and prognostic applications, and designing personalized therapeutic strategies and drug discovery. Furthermore, the platform may be enhanced by enriching the in situ cellular and subcellular resolution images with region-specific genomics and spatial transcriptomics data.

Figure 2:
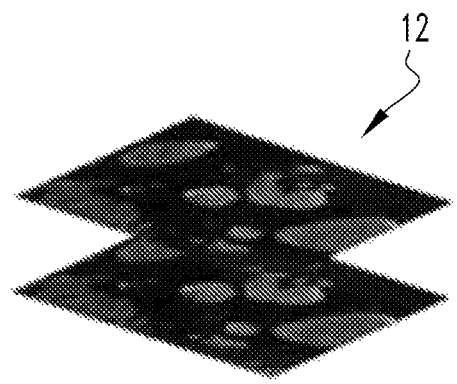
FIG. 2 is a schematic representation of an exemplary hyperplexed image stack.

FIG. 1 is a schematic diagram of an exemplary computational systems pathology spatial analysis (CSPSA) platform 5 for in situ multi-parameter cellular and sub-cellular Imaging data according to an embodiment of the disclosed concept in which the various methodologies described herein may be implemented. As seen in FIG. 1, CSPSA platform 5 is a computing device structured to receive and store certain multi-parameter cellular and subcellular imaging data 10 (such as for a large patient cohort including tumors from recurrent and non-recurring cancers, or for individual patients or individual tumors) and process such data 10 as described herein. In the non-limiting exemplary embodiment, multi-parameter cellular and subcellular imaging data 10 is generated using multiplexed or hyperplexed immunofluorescence imaging, although it will be understood that other imaging techniques, such as those described elsewhere herein, may also be used. For example, multi-parameter cellular and subcellular imaging data 10 may be based on the exemplary hyperplexed image stack 12 for all patient data in a cohort as represented in FIG. 2.

CSPSA platform 5 may be, for example and without limitation, a PC, a laptop computer, a tablet computer, a smartphone, or any other suitable computing device structured to perform the functionality described herein. CSPSA platform 5 includes an input apparatus 15 (such as a keyboard), a display 20 (such as an LCD), and a processing apparatus 25. A user is able to provide input into processing apparatus 25 using input apparatus 15, and processing apparatus 25 provides output signals to display 20 to enable display 20 to display information to the user (such as spatial maps or other spatial dependency images, microdomain images, weighted graph images and/or communication network graph images) as described in detail herein. Processing apparatus 25 comprises a processor and a memory. The processor may be, for example and without limitation, a microprocessor (µP), a microcontroller, an application specific integrated circuit (ASIC), or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory has stored therein a number of routines that are executable by the processor, including routines for implementing the disclosed concept as described herein. In particular, processing apparatus 25 includes a spatial heterogeneity quantification component 30 configured for generating a global quantification of a spatial heterogeneity among cells of certain varying predetermined phenotypes in the multi-parameter cellular and subcellular imaging data 10 as described herein, a microdomain identification component 35 configured for identifying a plurality of microdomains as described herein for a plurality of tumor sections from the multi-parameter cellular and subcellular imaging data 10 and based on the global quantification generated by spatial heterogeneity quantification component 30, a weighted graph component 40 configured for constructing weighted graphs for the multi-parameter cellular and subcellular imaging data 10 as described herein, and a communications network component 45 configured for constructing communications network graphs for the multi-parameter cellular and subcellular imaging data 10 as described herein.

Figure 3:
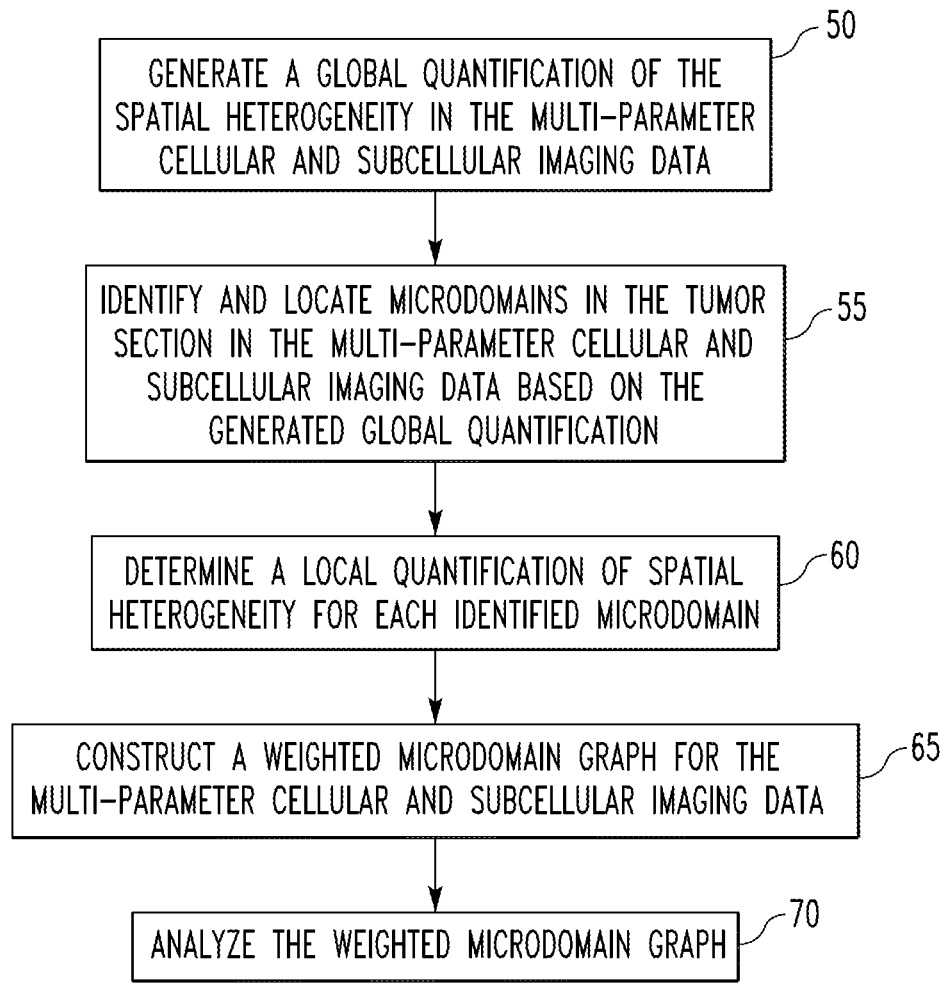
FIG. 3 is a flowchart illustrating a method of analyzing tumor progression/evolution from multi-parameter cellular and subcellular imaging data obtained from a plurality of tumor sections from a patient cohort that may be implemented in the CSPSA platform of FIG. 1 according to one exemplary embodiment of the disclosed concept.

FIG. 3 is a flowchart illustrating a method of analyzing tumor progression/evolution from multi-parameter cellular and subcellular imaging data 10 obtained from a plurality of tumor sections from a patient cohort that may be implemented in CSPSA platform 5 according to one exemplary embodiment of the disclosed concept. It will be understood, however, that this is meant to be exemplary only, and that the steps of the method shown in FIG. 3 can be implemented in other configurations and/or platforms.

Figure 4:
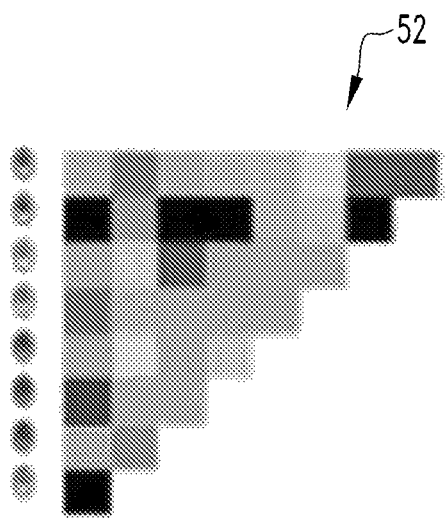
FIG. 4 is a schematic representation of an exemplary global spatial map.
Figure 5:
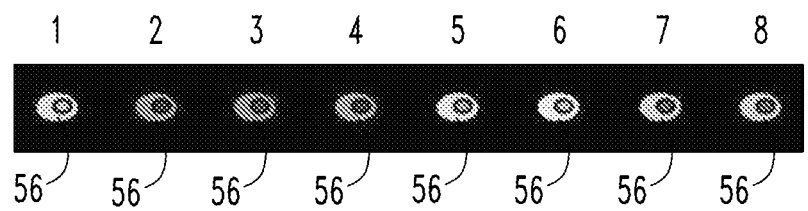
FIG. 5 shows a schematic representation of each of the predetermined dominant biomarker intensity patterns of the exemplary embodiment of the disclosed concept.
Figure 6:
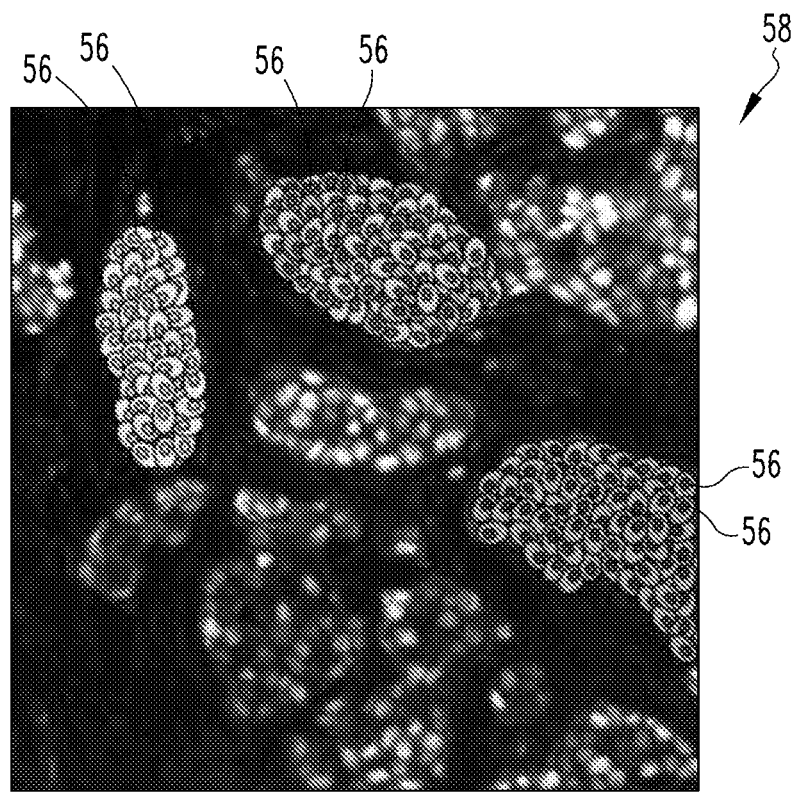
FIG. 6 shows a schematic representation of a cell spatial dependency image according to one particular exemplary embodiment of the disclosed concept.

The method begins at step 50, wherein spatial heterogeneity quantification component 30 generates a global quantification of the spatial heterogeneity in multi-parameter cellular and subcellular imaging data 10. In the exemplary embodiment, the global quantification generated in step 50 is a global spatial map for the multi-parameter cellular and subcellular imaging data 10. In one particular implementation, the global spatial map is a global PMI map 52 as shown in FIG. 4 that is generated in the manner described in PCT Application No. PCT/US2016/036825 and United States Patent Application Publication No. 2018/0204085 mentioned elsewhere herein and incorporated herein by reference. In this exemplary implementation, multi-parameter cellular and subcellular imaging data 10 is created by generating a number of biomarker images from a number of a sections of tissue by labelling each section of tissue with multiple, different biomarkers (e.g., ER, PR, and HER2). As discussed in the aforementioned applications, PMI map 52 is generated by first performing cell segmentation on the multi-parameter cellular and subcellular imaging data 10 (i.e., on each of the "slide" thereof). Any of a number of known or hereafter developed suitable cell segmentation algorithms may be employed. Then, spatial location and biomarker intensity data for each cell is obtained, and each cell is assigned to one of a predetermined phenotypes (each phenotype being a predetermined dominant biomarker intensity pattern) based on the biomarker intensity composition of the cell. FIG. 5 shows a schematic representation 56 of each of the predetermined dominant biomarker intensity patterns, labeled 1 through 8, of the exemplary embodiment. In the exemplary embodiment, each schematic representation 56 is provided in a unique color or colors so as to enable the schematic representations to be readily distinguishable from one another. The cell assignments just described and the schematic representations shown in FIG. 5 may be used to generate a cell spatial dependency image which visually demonstrates the heterogeneity of the subject tissue samples. FIG. 6 shows a cell spatial dependency image 58 according to one particular exemplary embodiment of the disclosed concept. As seen in FIG. 6, cell spatial dependency image 58 shows spatial dependencies among the cells of the subject slides using the schematic representations 56. Next, a spatial network is constructed to describe the organization of the dominant biomarker intensity patterns in the subject slide(s). Then, the heterogeneity of the subject slides is quantitated by generating a PMI map 52 as shown FIG. 4. In the exemplary embodiment, the spatial network and the PMI map 52 are generated as set forth below.

In order to represent the spatial organization of the biomarker patterns in the biomarker image (i.e., the tissue/tumor sample) of the subject slides, a network is constructed for the subject slides. The construction of spatial networks for tumor samples intrinsically couples cellular biomarker intensity data (in the nodes of the network) to spatial data (in the edges of the network). The assumptions in the network construction are that cells have the ability to communicate with nearby cells up to a certain limit, e.g., up to 250 µm, and that the ability for cells to communicate within that limit is dependent upon cellular distance. Therefore, the probability distribution in the exemplary embodiment is computed for the distance between a cell in the subject slide and its 10-nearest neighbors. A hard limit was chosen based on the median value of this distribution times 1.5 (to estimate the standard deviation), where cells in the network were connected only within this limit. Then, the edges between cells in the network are weighted by the distance between the adjacent cells.

Next, in the exemplary embodiment, pointwise mutual information (PMI) is used to measure the association between each pair of biomarker patterns in the dictionary, and thus different cell phenotypes, for the subject slides. This metric captures general statistical association, both linear and nonlinear, where previous studies have used linear metrics such as Spearman's rho coefficient. Once PMI is computed for each pair of biomarker patterns, a measure of all associations in the data of the subject slide is displayed in a PMI map 52. It will be appreciated that the use of PMI in this embodiment is exemplary only, and that other methods that define spatial relationships, such as, without limitation, those described in Spagnolo D M, Al-Kofahi Y, Zhu P, Lezon T R, Gough A, Stern A M, Lee A V, Ginty F, Sarachan B, Taylor D L, Chennubhotla S C, *Platform for Quantitative Evaluation of Spatial Intratumoral Heterogeneity in Multiplexed Fluorescence Images*, Cancer Res. 2017 Nov. 1, and Nguyen, L., Tosun, B., Fine, J., Lee, A., Taylor L., Chennubhotla, C. (2017), *Spatial statistics for segmenting histological structures in H&E stained tissue images*, IEEE Trans Med Imaging. 2017 Mar. 16, may be employed in connection with the disclosed concept.

The exemplary PMI map 52 describes relationships between different cell phenotypes within the microenvironment of the subject slides. In particular, the entries in PMI map 52 indicate how frequently a particular spatial interaction between two phenotypes (referenced by the row and column number) occurs in the dataset when compared to the interactions predicted by a random (or background) distribution over all phenotypes. Entries in a first color, such as red, denote a strong spatial association between phenotypes, while entries in a second color, such as black, denote a lack of any co-localization (weak spatial association between phenotypes). Other colors may be used to denote other associations. For example, PMI entries colored in a third color, such as green, denote associations that are no better than a random distribution of cell phenotypes over the entire dataset. Additionally, PMI map 52 can portray anti-associations with entries denoted in a fourth color, such as blue (e.g., if phenotype 1 rarely occurs spatially near phenotype 3).

Figure 7:
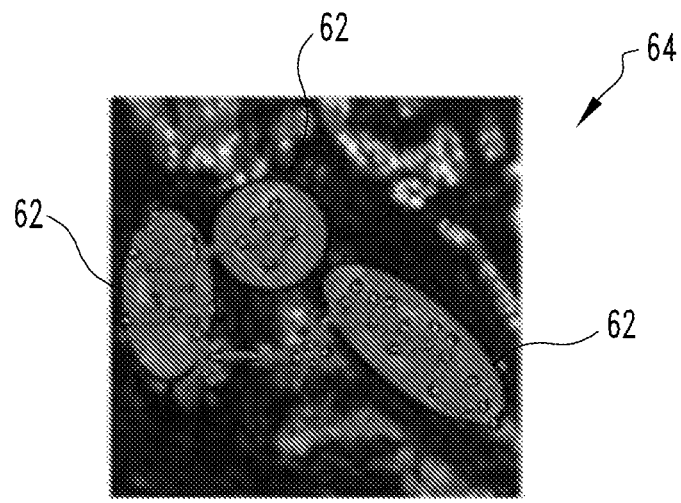
FIG. 7 is a schematic representation of exemplary microdomains in an exemplary tissue section according to one exemplary embodiment of the disclosed concept.

Referring again to FIG. 3, following step 50, the method then proceeds to step 55. At step 55, microdomain identification component 35 identifies and locates one or more microdomains (e.g., as described elsewhere herein) in each of the tumor sections in the multi-parameter cellular and subcellular imaging data 10 based on the global quantification generated at step 50. For example, a cancer cell type and a specific immune cell type that co-localizes with it may have a high spatial co-occurrence value. Using the cancer-immune cell combination as a seed point and mining the global quantification (e.g., spatial map) to propagate phenotypic associations, in any given tissue section, microdomains can be generated by growing a spatial network of cells around the seed based on a distance cutoff (say ~100 cells). Such exemplary microdomains 62 are illustrated in the exemplary tissue section 64 shown in FIG. 7.

Next, at step 60, a local quantification of spatial heterogeneity (e.g., a local spatial map such as a local PMI map) is determined for each microdomain identified in step 55. In addition, each of the determined local quantifications in each tissue section is used to define a degree of similarity between pairs of microdomains in the tissue section. In particular, in the exemplary embodiment, given two microdomains A and B, a distance function is defined that is a combination of (i) the difference in the relative abundance of cells in the microdomains A and B and (ii) the difference in their local quantifications (e.g., local spatial maps such as $PMI_A$ and $PMI_B$, although, as noted herein, other methods may also be used). This procedure is repeated for every pair of microdomains across all of the multi-parameter cellular and subcellular imaging data 10. This process will result in a weighted similarity being determined for each pair of microdomains in each tissue section.

Figure 8:
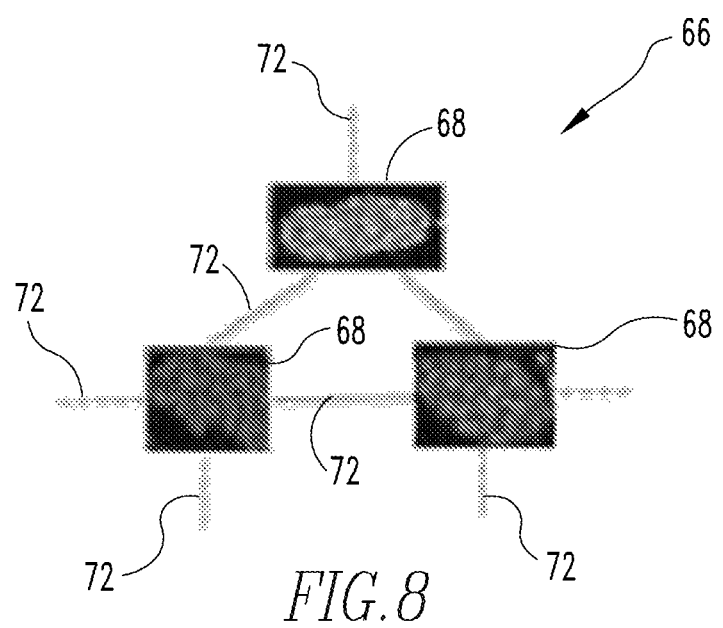
FIG. 8 is a schematic representation of a weighted microdomain graph constructed for multi-parameter cellular and subcellular imaging data according to one exemplary embodiment of the disclosed concept.

Next, at step 65, a weighted microdomain graph 66 shown in exemplary form in FIG. 8 is constructed for multi-parameter cellular and subcellular imaging data 10. Each node 68 in weighted microdomain graph 66 is one of the microdomains generated in step 55, and the edges 72 connecting each pair of microdomains are weighted by their determined similarity (e.g., the weighted similarity value as described above). Weighted microdomain graph 66 may then be displayed on display 20.

Then, as shown in step 70 of FIG. 3, the weighted microdomain graph 66 may be further analyzed to understand the progression of phenotypes during the process of metastasis. Note that there is a ground truth label for each entire tissue section in multi-parameter cellular and subcellular imaging data 10 as coming from either a recurrent (R) or non-recurrent (NR) patient, but apriori, knowledge is not available to ascertain which microdomains discriminate the two categories the most. In the exemplary embodiment, the labels R and NR are transferred from tissue sections to the corresponding microdomains. A few iterations of belief propagation are then run to refine the labels, and then isolate cliques of microdomains on weighted microdomain graph 66 that are either uniformly R or NR. With improved confidence on the label assignment, a betweenness centrality measure can be used to identify the microdomains that are most commonly traversed on the path from NR to R. To mimic evolutionary trajectories, random walks on weighted microdomain graph 66 can be undertaken, knowing that some microdomains are to be found exclusively in either the observed or unobserved metastasized data. Relative probabilities of paths from NR to R can be compared to identify classes of events that are important in metastasis. The mean first passage times of the random walks may then be used to identify microdomains with propensity to metastasis as the set of nodes from which the probability of a random walk reaching either R or NR is 0.5. Note that the microdomains with metastatic potential are the mid points in the evolutionary trajectory from NR to R. In the exemplary embodiment, the steps just described will be performed by a component of the CSPSA platform 5, with the results being displayed to the user on display 20 of CSPSA platform 5. Thus, this aspect of the disclosed concept provides the ability to define, identify and compare phenotypes ("phenotypic evolution") that are important to metastasis as described herein. In addition, it will be appreciated that cancer is just one example area to which the disclosed concept may be applied, and that the disclosed concept may also be applied to other disease tissues, such neurodegenerative diseases, metabolic diseases, and inflammatory diseases, among others.

Figure 9:
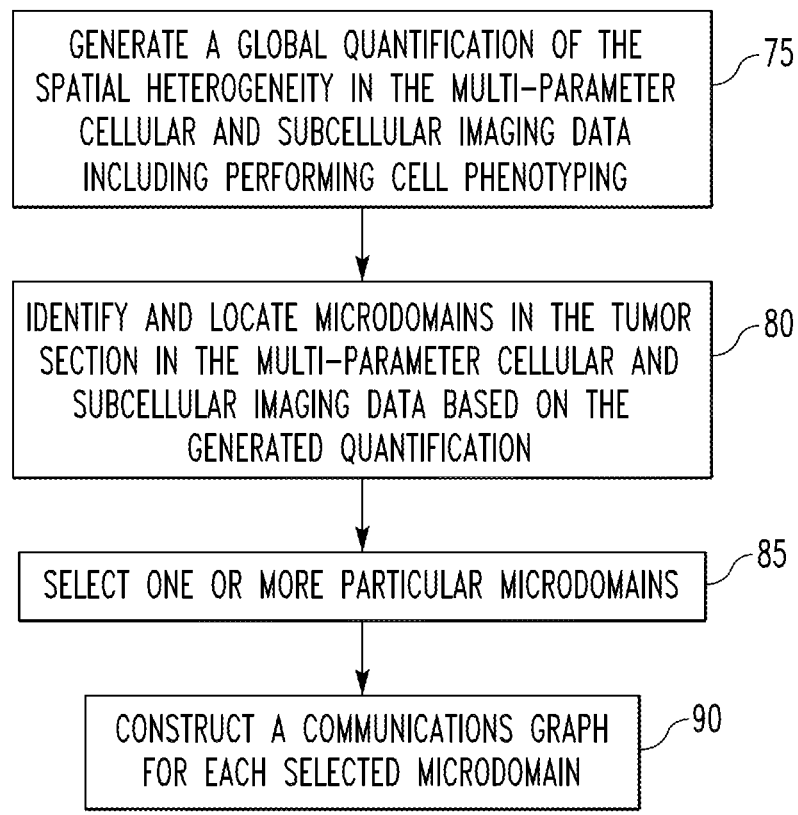
FIG. 9 is a flowchart illustrating a method of generating a representation of spatially informed heterocellular communication from multi-parameter cellular and subcellular imaging data according to another exemplary embodiment of the disclosed concept.

FIG. 9 is a flowchart illustrating a method of generating a representation of spatially informed heterocellular communication from multi-parameter cellular and subcellular imaging data 10, which in this embodiment is obtained from a number of tumor sections from a patient, that may be implemented in CSPSA platform 5 according to another exemplary embodiment of the disclosed concept. It will be understood, however, that this is meant to be exemplary only, and that the steps of the method shown in FIG. 9 can be implemented in other configurations and/or platforms.

The method begins at step 75, wherein spatial heterogeneity quantification component 30 generates a quantification of the spatial heterogeneity in the multi-parameter cellular and subcellular imaging data 10 as described in detail elsewhere herein. As noted elsewhere herein, the quantification of the spatial heterogeneity performed in step 75 includes performing cell phenotyping on the multi-parameter cellular and subcellular imaging data 10 to identify the certain varying predetermined phenotypes. In the exemplary embodiment, the quantification generated in step 75 is a spatial map for the multi-parameter cellular and subcellular imaging data 10. In one particular implementation, the spatial map is generated in the manner described in PCT Application No. PCT/US2016/036825 and United States Patent Application Publication No. 2018/0204085 mentioned elsewhere herein and incorporated herein by reference. In this exemplary implementation, the multi-parameter cellular and subcellular imaging data 10 is created by generating a number of biomarker images from a number of a sections of tissue by labelling each section of tissue with multiple, different biomarkers (e.g., ER, PR, and HER2). In the non-limiting exemplary embodiment, multi-parameter cellular and subcellular imaging data 10 is generated using multiplexed or hyperplexed immunofluorescence imaging, although it will be understood that other imagine techniques, such as those described elsewhere herein, may also be used.

Next, at step 80, microdomain identification component 35 identifies and locates one or more microdomains as described herein in each of the tumor sections in the multi-parameter cellular and subcellular imaging data 10 based on the quantification generated at step 75. Then, at step 85, one or more of the identified microdomains is selected. The method then proceeds to step 90.

Figure 10:
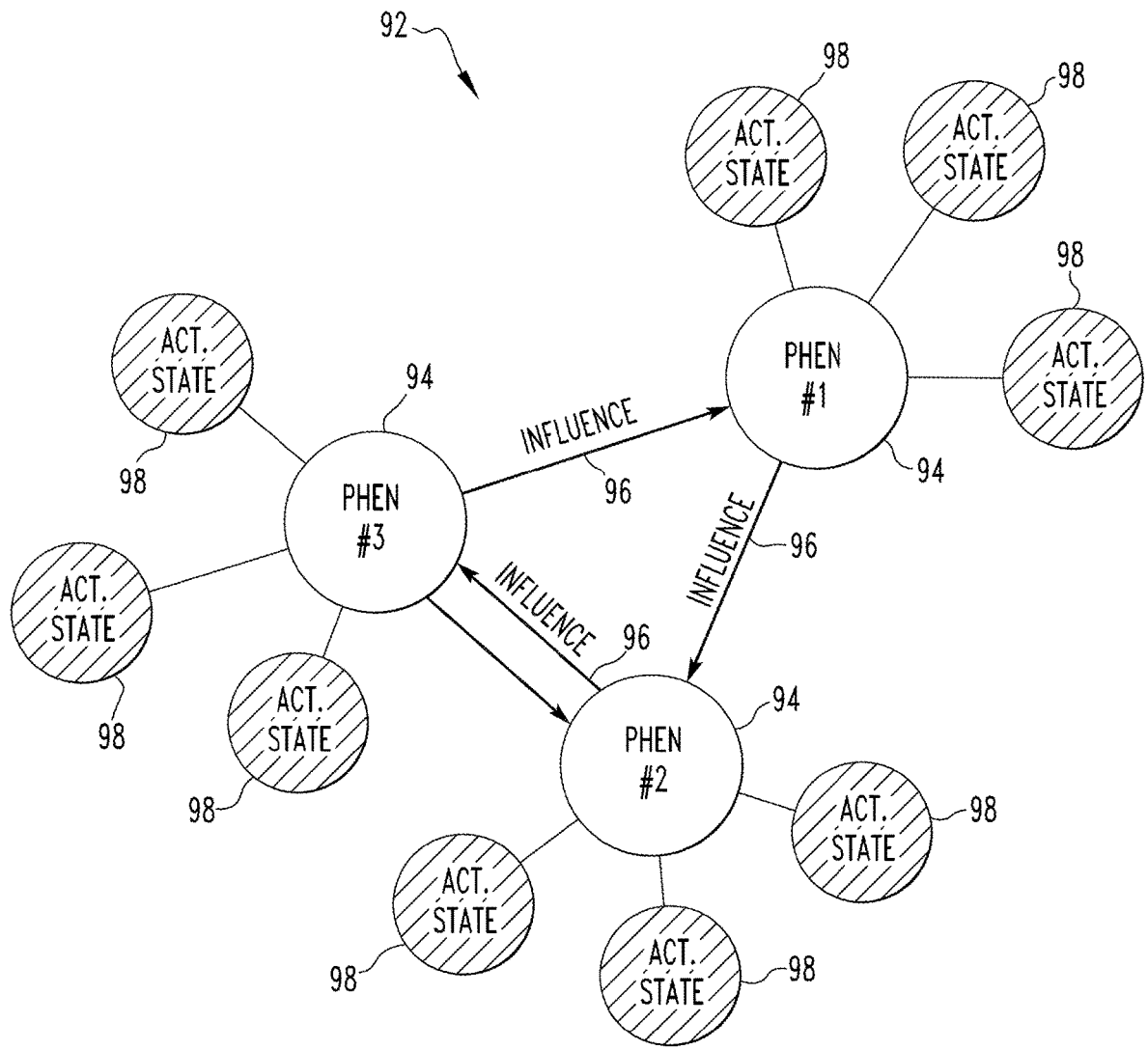
FIG. 10 is a schematic representation of an exemplary communications graph according to one exemplary embodiment of the disclosed concept.

At step 90, communications network component 45 constructs a communications graph for each of the selected microdomains. The communications graphs may be displayed on display 20. An exemplary communications graph 92 is shown in FIG. 10. As seen in FIG. 10, in the exemplary embodiment, each of the phenotypes is a node 94 in communications graph 92, and the edge 96 between each pair of the phenotypes (each pair of nodes 94) in communications graph 92 is indicative of an influence of one phenotype in the pair on the presence of the other phenotype in the pair. In the exemplary embodiment, each phenotype (each node 94) in communications graph 92 is represented by a data vector obtained from the multi-parameter cellular and subcellular imaging data 10. Also, the edges 96 in communications graph 92 in the exemplary embodiment are generated, for each pair of the phenotypes, by establishing a numerical relationship between the phenotypes in the pair by determining a linear or non-linear correlation coefficient value between the data vectors of the phenotypes in the pair (after removing any confounding effects of phenotypes other than the phenotypes in the pair). In addition, a directionality is established for each of the numerical relationships, preferably based on a number of receptor-ligand databases for the relevant biomarkers. Thus, in this embodiment, the edge 96 between each pair of nodes 94 is indicative of the determined numerical relationship and the determined directionality. In the exemplary embodiment, the edges 96 may be colored to represent certain correlation coefficient values (e.g., degrees of positive or negative correlation).

In addition, in the exemplary embodiment, each data vector of each node 94 is a vector of expression values for a number of predetermined biomarkers, wherein the predetermined biomarkers are the particular biomarkers that were used in generating the multi-parameter cellular and subcellular imaging data 10. For example, each vector of expression values may be a biomarker intensity pattern for the predetermined biomarkers determined at step 75. Each data vector may also be analyzed and biologically interpreted to determine a number of states of activation 98 for each of the phenotypes (each node 94), which states of activation 98 are included in the communications graph 92. For example, biomarker ALDH1 is a surrogate for sternness of a tumor cell, and biomarker PD-L1 determines the mutational burden.

Figure 11:
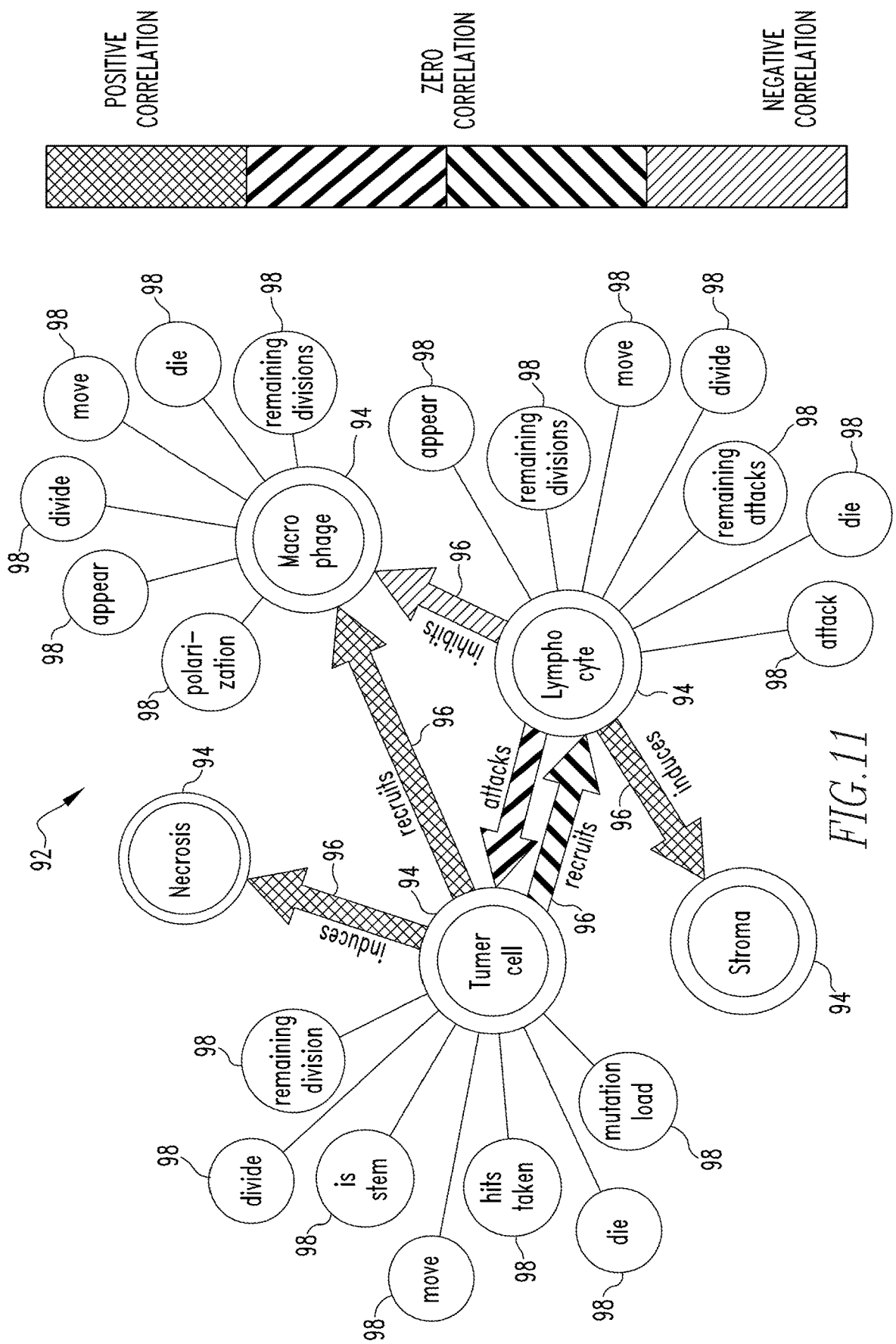
FIG. 11 is a schematic diagram of a particular communications graph generated according to a particular exemplary embodiment wherein the phenotypes are tumor cell, lymphocyte, macrophage, stroma and necrosis.

FIG. 11 is a schematic diagram of a particular communications graph 92 generated according to a particular exemplary embodiment wherein the phenotypes (nodes 94) are tumor cell, lymphocyte, macrophage, stroma and necrosis. Various edge influences 96 and various states of activation 98 are also shown.

One outcome of the mapping described herein is inferring pathways of disease progression based on the local tumor micro-environment (TME) and subsequently listing the known molecular targets in the pathway. Subsequent to this, machine learning tools (e.g. Balestra Web) can be used to predict drug target interactions based on spatial relationships. This can lead to drug repurposing, as well as novel therapeutic development. Moreover, described in detail below are a number of exemplary particular clinical applications which may incorporate various aspects of the disclosed concept (e.g., applications of CSPA platform 5), including: (1) drug discovery and personalized medicine strategies with spatially modulated computational systems pathology, (2) a cancer/disease landscape which is a geometrical representation of a multi-parametric readout of a patient's cancer/disease status, and (3) application of the CSPA platform for in-vitro models for basic research and clinical translation.

In one particular exemplary embodiment, the disclosed concept may be used for drug discovery and personalized medicine strategies with spatially modulated computational systems pathology. More specifically, spatial intra-tumoral heterogeneity is a key aspect in the determination of cancer time evolution and patient fate. This heterogeneity is reflected in the diversity of the heterocellular communication networks embedded in the microdomains and thus the resulting systems biology is patient dependent. Current therapeutic strategies are designed for the average patient and hence do not reflect the systems biology that is unique to a patient. Patient-specific systems pathology begins with the identification of microdomains/regions of interest, characterization of the underlying communication networks, and quantifying the interdependency of microdomains in space and time accurately. This knowledge is also essential for novel drug design strategies. This strategy can also be enhanced with the use of region specific genomics.

Figure 12:
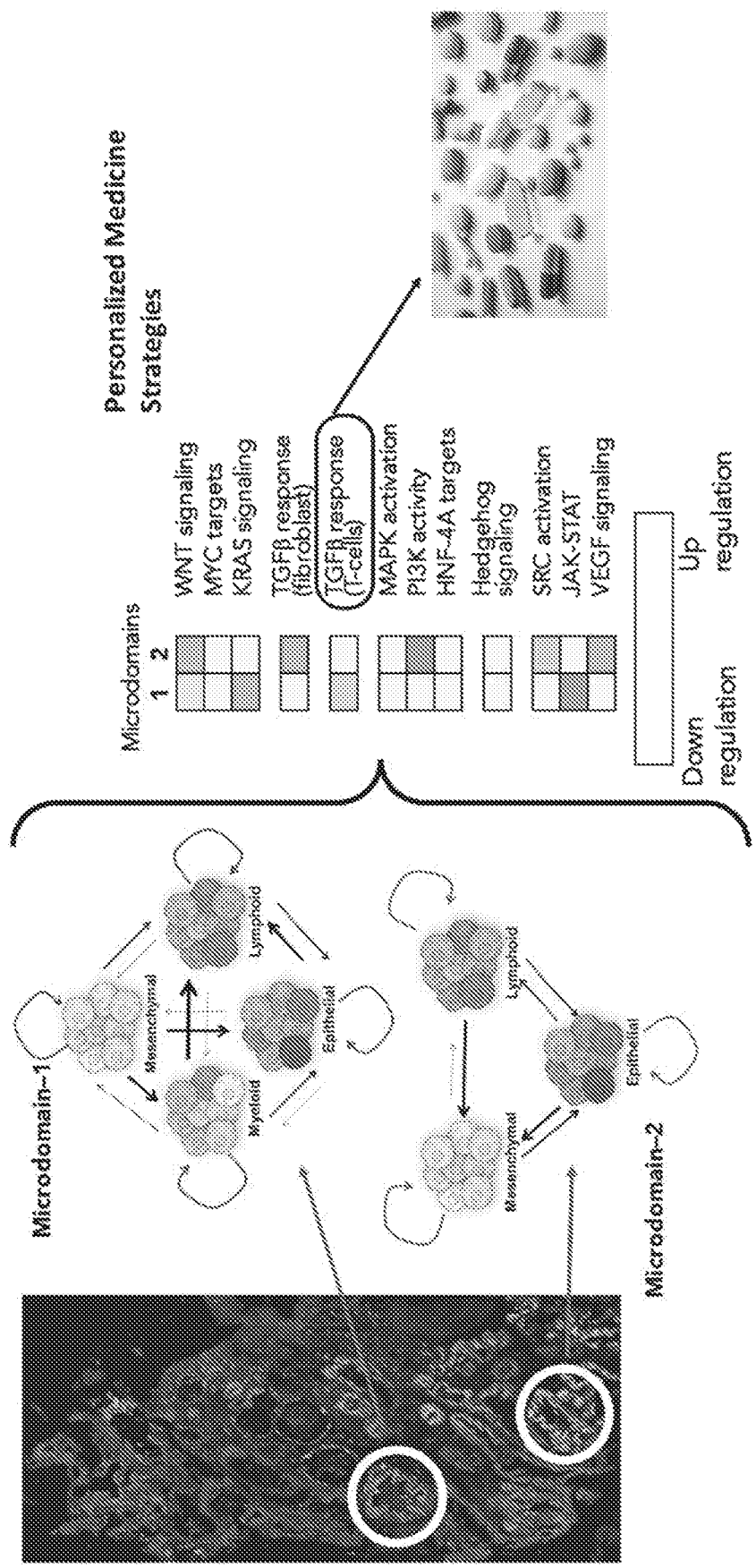
FIG. 12 is a schematic representation of a personalized medicine strategy according to an aspect of the disclosed concept.

FIG. 12 is a schematic representation of a personalized medicine strategy according to this aspect of the disclosed concept, which extends from tissue section to personalized therapeutic treatments. FIG. 12 shows, from left to right, i) a multiparameter image at cellular/subcellular resolution, ii) identification of regions of interest (mircodomains) in the image, iii) reconstruction of the intra-microdomain communication networks with specific connection weights and the spatial relation between cells/microdomains, iv) combining the information to extract the precise systems biology, and v) definition of a personalized therapeutic strategy.

As seen in FIG. 12, in the illustrated exemplary embodiment, for an individual patient, sample microdomains 1 and 2 were found to be phenotypically distinct. For this tissue sample, a cellular phenotyping algorithm as described herein is applied. Next, heterocellular networks are constructed for each microdomain as described herein. A prognostic test applied separately on microdomains 1 and 2 reveals that both microdomains are a low risk for recurrence. However, when those microdomains are in close proximity, the risk of recurrence becomes dramatically higher, suggesting a flow of information between microdomains 1 and 2. Thus, in this aspect to the disclosed concept, the heterocellular networks inform which pathways are activated and what the relationship is between the two networks. For example, WNT signaling is up regulated in microdomain 2 but down regulated in microdomain 1, and TGFE3 is up regulated in microdomain 1 but down regulated in microdomain 2. In this aspect of the disclosed concept, the pathways and microdomain networks are identified, and hence the information flow that has to be inhibited to slow down cancer progression for specific individuals is likewise identified. With this information, a personalized medicine strategy can be designed.

In another particular exemplary embodiment, the disclosed concept may be used for precisely describing the time evolution of a disease such as cancer in a specific patient. The disclosed concept thus defines a cancer landscape which is a geometrical representation of a multiparametric readout of a patient's cancer status. Each point in the cancer landscape represents the cancer status of the patient, such as pre-cancerous, early stage, invasive, etc. The path followed on this landscape describes the temporal evolution of the disease for that specific patient. The current therapeutic practice uses a cancer landscape averaged over the patient population. Unless the individual patient profile matches the average profile exactly, the predictions done with the average model can be inaccurate.

Figure 13:
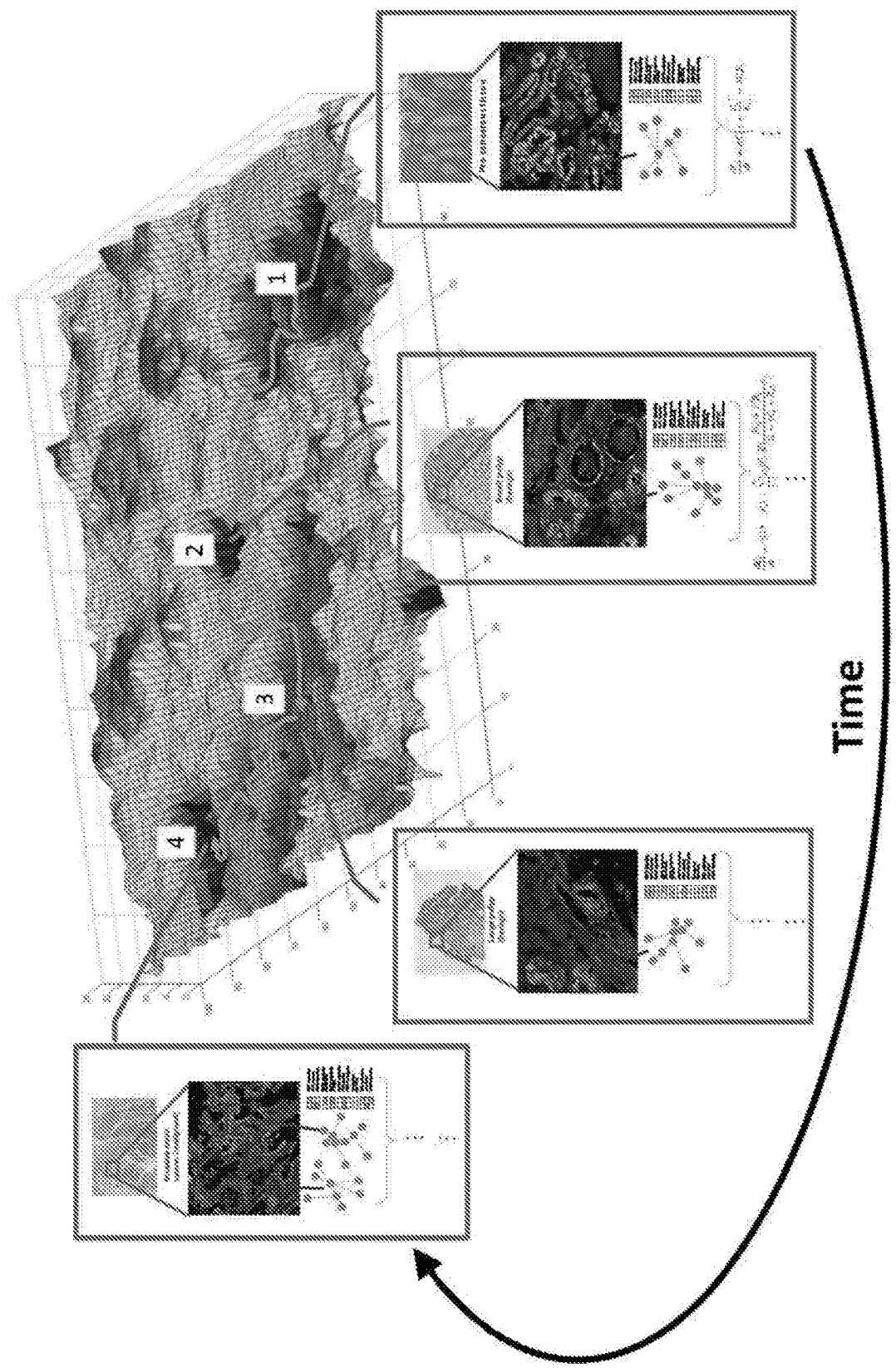
FIG. 13 is a schematic representation of an exemplary cancer landscape according to an aspect of the disclosed concept.

FIG. 13 shows an exemplary cancer landscape comprising a geometrical representation wherein locations on the landscape represent the status of a specific exemplary patient. FIG. 13 uses colon cancer progression as an example, wherein the basin with label 1 represents the pre-cancerous status, the basin with label 2 represents the small polyp status, the basin with label 3 represents the large polyp status, and the basin with label 4 represents the invasive colon cancer status. The arrows within the geometrical representation show the path followed by the patient from pre-cancerous to invasive cancer. From this model, the dynamics of the cancer evolution can be inferred.

According to an aspect of this embodiment of the disclosed concept, a retrospective patient cohort is sued to build a comprehensive library of microdomains as described herein for tissue evolution from pre-cancerous to metastasis. Specific heterocellular communication networks as described herein are associated to each microdomain. In addition, each heterocellular communication network has a systems biology model which takes the form of a system of ordinary differential equations. The system of ordinary differential equations defines the kinetics of the cancer landscape. For prospective studies, the kinetics help to predict the temporal evolution of microdomains from pre-cancerous to metastasis. In addition, the kinetic models are a proxy to generative models of synthetic tissues.

In still another particular exemplary embodiment, the disclosed concept may be used in conjunction with in-vitro models for basic research and clinical translation. More specifically, in the two particular applications of the disclosed concept described immediately above, the platform of the disclosed concept was applied to in situ hyperplexed single cell resolution solid tumor images. In the present embodiment, the same platform is applied to image data from in vitro microphysiological models. Multicellular in vitro models permit the study of spatio-temporal cellular heterogeneity and heterocellular communication that recapitulates human tissue that can be applied to investigate the mechanisms of disease progression in vitro, to test drugs and to characterize the structural organization and content of these models for potential use in transplantation.

In vitro models come in the form of 2D cultures, 3D spheroids, organoids and biomimetic microphysiology systems. The goal of these systems has been to get closer to physiologically relevant biomimetics. 2D cultures are cell cultures that grow on a adhesion surface. They develop a 2D communication network and hence the exchange of information is limited to two dimensions. 3D Spheroids are clusters of cells that grow in space. Although cells are grown in an artificial environment, they mimic better the in vivo growth conditions because the cells are allowed to interact and grow in all directions. Organoids are very small but self-organized three-dimensional tissue cultures. They are usually derived from stem cells. Organoids can be crafted to replicate much of the complexity of an organ, or can be guided to express selected aspects of it like producing only certain types of cells. The reproduction of the organ function, even if partial, implies the reproduction of the systems biology and heterocellular communication in in vitro controlled conditions. Biomimetic microphysiology systems are a step forward in mimicking organ functions with respect to organoids. A 3D microfluidic channel cell culture chip mimics all activities, mechanics and physiological response of entire organs. This allow a more accurate representation of the systems biology and heterocellular communication network.

In one or more aspects of this particular embodiment, the spatio-temporal cellular heterogeneity and heterocellular communication may be monitored by building a timeline of images and comparing the evolution of the inferred networks in the models. The level of complexity of in vitro systems from 2D cultures to biomimetic MPS is reflected in the complexity of the systems biology models that can be developed. Although applicable to all of the possible in vitro models, the biomimetic models that are constructed by layering or bioprinting different cell types in the proper 3D organization will benefit the most by defining the spatial relationships within the model. The same type of systems pathology defined in the two particular applications of the disclosed concept described immediately above will be valid here. The goal is to demonstrate that the in vitro models reflect the organization and spatial relationships identified in situ tissue/organs under investigation and that the systems biology can be recapitulated in vitro. The models may be established and either studied under "normal" healthy conditions, or established as disease models using cells from patients with a disease and/or induced pluripotent stem cells (iPSCs) from patients that are differentiated and matured into the cell types required in the model. At distinct time points and after selected treatments, the models are fixed, embedded, sectioned and labeled just like tissue from a patient. Hyperplexed imaging modalities are then applied to the labeled tissue sections. The computational and systems pathology analyses of the disclosed concept described herein may then be applied to the tissue sections obtained from the models.

Finally, while the disclosed concept has been described in connection with imaging data obtained from tumor sections, it will be understood that the disclosed concept may also be applied to imaging data that is obtained from other types of tissue sections and/or from un-sectioned tissue samples using imaging modalities that can penetrate into solid, un-sectioned samples.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of analyzing a progression of a disease from multi-parameter cellular and subcellular imaging data obtained from a plurality of tissue samples from a plurality of patients or a number of multicellular in vitro models, comprising:
    generating a global quantification of a spatial heterogeneity among cells of certain varying predetermined phenotypes in the multi-parameter cellular and subcellular imaging data;
    identifying a plurality of microdomains for a plurality of tissue sections from the multi-parameter cellular and subcellular imaging data based on the global quantification, each microdomain being associated with a respective one of the tissue sections; and
    constructing a weighted graph for the multi-parameter cellular and subcellular imaging data, the weighted graph being indicative of a progression of the predetermined phenotypes and having a plurality of nodes and a plurality of edges each being located between a pair of the nodes, wherein in the weighted graph each node is a particular one of the microdomains and the edge between each pair of microdomains in the weighted graph is indicative of a degree of similarity between the pair of the microdomains, such that the weighted graph may be analyzed to understand the progression of the disease.

2. The method according to claim 1, further comprising for each pair of microdomains in the plurality of microdomains, determining a weighted similarity between the microdomains of the pair, wherein the edge between each pair of microdomains in the weighted graph is the weighted similarity determined for the pair of the microdomains.

3. The method according to claim 2, further comprising determining a local quantification of a spatial heterogeneity among cells for each of the identified microdomains, wherein the determining of the weighted similarity between the microdomains of each pair is based on the local quantification of each microdomains of the pair.

4. The method according to claim 1, wherein the global quantification is a spatial map for the multi-parameter cellular and subcellular imaging data.

5. The method according to claim 4, wherein the spatial map is a pointwise mutual information (PMI) map.

6. The method according to claim 1, wherein the predetermined phenotypes comprise a predetermined set of dominant biomarker intensity patterns.

7. The method according to claim 1, wherein a number of the identified microdomains are associated with an outcome specific variable that is in the form of time to recurrence or that is indicative of disease progression.

8. The method according to claim 7, wherein the tissue samples are tumor samples and wherein the outcome specific variable is indicative of metastatic potential.

9. A non-transitory computer readable medium storing one or more programs, including instructions, which when executed by a computer, causes the computer to perform the method of claim 1.

10. A computerized system for analyzing a progression of a disease from multi-parameter cellular and subcellular imaging data obtained from a plurality of tissue samples from a plurality of patients or a number of multicellular in vitro models, comprising:
    a processing apparatus, wherein the processing apparatus includes:
        a spatial heterogeneity quantification component configured for generating a global quantification of a spatial heterogeneity among cells of certain varying predetermined phenotypes in the multi-parameter cellular and subcellular imaging data;
        a microdomain identification component configured for identifying a plurality of microdomains for a plurality of tissue sections from the multi-parameter cellular and subcellular imaging data based on the global quantification, each microdomain being associated with a respective one of the tissue sections; and
        a weighted graph component configured for constructing a weighted graph for the multi-parameter cellular and subcellular imaging data, the weighted graph being indicative of a progression of the predetermined phenotypes and having a plurality of nodes and a plurality of edges each being located between a pair of the nodes, wherein in the weighted graph each node is a particular one of the microdomains and the edge between each pair of microdomains in the weighted graph is indicative of a degree of similarity between the pair of the microdomains, such that the weighted graph may be analyzed to understand the progression of the disease.

11. The system according to claim 10, wherein the weighted graph component is further configured for determining, for each pair of microdomains in the plurality of microdomains, a weighted similarity between the microdomains of the pair, wherein the edge between each pair of microdomains in the weighted graph is the weighted similarity determined for the pair of the microdomains.

12. The system according to claim 11, wherein the weighted graph component is further configured for determining a local quantification of a spatial heterogeneity among cells for each of the identified microdomains, wherein the determining of the weighted similarity between the microdomains of each pair is based on the local quantification of each microdomains of the pair.

13. The system according to claim 10, wherein the global quantification is a spatial map for the multi-parameter cellular and subcellular imaging data.

14. The system according to claim 13, wherein the spatial map is a pointwise mutual information (PMI) map.

15. The system according to claim 10, wherein the predetermined phenotypes comprise a predetermined set of dominant biomarker intensity patterns.

16. The system according to claim 10, wherein a number of the identified microdomains are associated with an outcome specific variable that is in the form of time to recurrence or that is indicative of disease progression.

17. The system according to claim 16, wherein the tissue samples are tumor samples and wherein the outcome specific variable is indicative of metastatic potential.

18. The system according to claim 10, further comprising a component configured for guiding therapeutic strategy based on identifying cell types and states of activation and evolution based on the weighted graph.

* * * * *